United States Patent [19]

O'Callaghan et al.

[11] Patent Number: 4,464,368

[45] Date of Patent: Aug. 7, 1984

[54] CEPHALOSPORIN ANTIBIOTICS

[75] Inventors: Cynthia H. O'Callaghan, Gerrards Cross; Barry E. Ayres, Ickenham; Christopher E. Newall, London; David G. H. Livermore, Princes Risborough; Derek R. Sutherland, Chalfont St. Giles, all of England

[73] Assignee: Glaxo Group Limited, London, England

[21] Appl. No.: 285,966

[22] Filed: Jul. 23, 1981

Related U.S. Application Data

[63] Continuation of Ser. No. 172,952, Jul. 28, 1980, abandoned, which is a continuation of Ser. No. 94,087, Nov. 14, 1979, abandoned.

[30] Foreign Application Priority Data

Nov. 15, 1978 [GB] United Kingdom ............... 44595/78
Nov. 15, 1978 [GB] United Kingdom ............... 44597/78

[51] Int. Cl.³ ................. C07D 501/38; A61K 31/425
[52] U.S. Cl. .................................... 424/246; 544/22; 544/25
[58] Field of Search .................. 544/22, 26, 27, 21; 424/246

[56] References Cited

U.S. PATENT DOCUMENTS

| 3,971,778 | 7/1976 | Cook et al. | 260/243 C |
| 4,017,515 | 4/1977 | Cook et al. | 260/332.3 R |
| 4,024,133 | 5/1977 | Cook et al. | 260/243 C |
| 4,024,137 | 5/1977 | Cook et al. | 260/243 C |
| 4,032,950 | 7/1977 | Cook et al. | 260/243 C |
| 4,060,686 | 11/1977 | Bradshaw et al. | 544/22 |
| 4,064,346 | 12/1977 | Cook et al. | 544/30 |
| 4,079,178 | 3/1978 | Cook et al. | 544/25 |
| 4,091,209 | 5/1978 | Cook et al. | 544/16 |
| 4,092,477 | 3/1978 | Cook et al. | 544/26 |
| 4,093,803 | 6/1978 | Cook et al. | 544/27 |
| 4,095,021 | 6/1978 | Bradshaw et al. | 544/22 |
| 4,098,888 | 7/1978 | Ochiai et al. | 424/246 |
| 4,103,084 | 7/1978 | Bradshaw et al. | 544/22 |
| 4,144,392 | 3/1979 | Bradshaw et al. | 544/27 |
| 4,144,393 | 3/1979 | Bradshaw et al. | 544/28 |
| 4,152,432 | 5/1979 | Heymes et al. | 424/246 |
| 4,162,360 | 7/1979 | Bradshaw et al. | 544/16 |
| 4,165,430 | 8/1979 | Bradshaw et al. | 544/22 |
| 4,166,115 | 8/1979 | Takaya et al. | 424/246 |
| 4,307,233 | 12/1981 | Farge et al. | 544/22 |
| 4,358,448 | 11/1982 | Payne et al. | 544/22 |
| 4,382,932 | 5/1983 | Lunn et al. | 544/22 |

FOREIGN PATENT DOCUMENTS 772030 3/1977 South Africa .
781870 3/1978 South Africa .
782168 3/1978 South Africa .
781630 3/1978 South Africa .
781502 3/1978 South Africa .
1399086 6/1975 United Kingdom .
1496757 1/1978 United Kingdom .

OTHER PUBLICATIONS

Tsuchiya et al., Antimicrobial Agents & Chemotherapy, 14 (4) 557–560 (1978).
Numata et al., J. Antibiotics XXXI (12) 1262–1271 (1970).
C. R. Acad. Sc. 284 1847 (1977) Heymes et al. English Abstract.
Heymes et al., Tetrahedron 34 2233–2243 (1978).
Hamilton-Miller et al., Jour. Antimicrobial Chemotherapy 4437–4444 (1978).
Chem. Pharm. Bull. 25 (11) 3115–3118 (1977).

Primary Examiner—Nicholas S. Rizzo
Attorney, Agent, or Firm—Bacon & Thomas

[57] ABSTRACT

Cephalosporin antibiotics of general formula

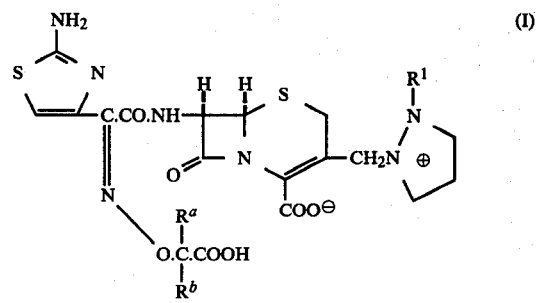

(wherein $R^a$ and $R^b$, which may be the same or different, each represent a $C_{1-4}$ alkyl group, or together with the carbon atom to which they are attached form a $C_{3-7}$ cycloalkylidene group and $R^1$ represents a $C_{1-4}$ alkyl group) exhibit broad spectrum antibiotic activity, the activity being unusually high against gram-negative organisms such as strains of Pseudomonas organisms.

Particularly effective compounds of formula (I) are (6R,7R)-7-[(Z)-2-(2-aminothiazol-4-yl)-2-(2-carboxyprop-2-oxyimino)acetamido]-3-(2-methylpyrazolium-1-ylmethyl)ceph-3-em-4-carboxylate and (6R,7R)-7-[(Z)-2-(2-aminothiazol-4-yl)-2-[(1-carboxycyclobut-1-oxyimino)acetamido]-3-(2-methylpyrazolium-1-ylmethyl)]ceph-3-em-4-carboxylate. The invention also includes the non-toxic salts and non-toxic metabolically labile esters of compounds of formula (I), compositions containing the antibiotic compounds of the invention, and methods for combatting bacterial infections utilizing the antibiotics.

10 Claims, No Drawings

CEPHALOSPORIN ANTIBIOTICS

This application is a continuation of application Ser. No. 172,952 filed July 28, 1980, which is a continuation of Ser. No. 094,087, filed Nov. 14, 1979, both now abandoned.

The present invention provides cephalosporin antibiotics of the formula:

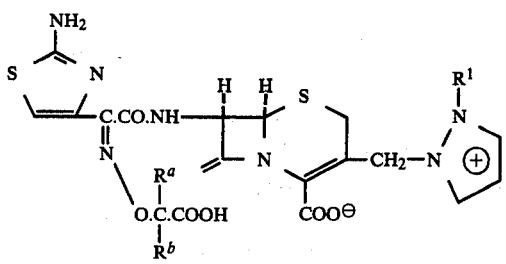

(wherein $R^a$ and $R^b$, which may be the same or different, each represents a $C_{1-4}$ alkyl group, preferably a straight chain alkyl group, i.e. a methyl, ethyl, n-propyl or n-butyl group and particularly a methyl or ethyl group, or, together with the carbon atom to which they are attached, form a $C_{3-7}$ cycloalkylidene group preferably a $C_{3-5}$ cycloalkylidene group; and $R^1$ represents a $C_{1-4}$ alkyl group, preferably a methyl group) and non-toxic salts and non-toxic metabolically labile esters thereof.

The cephalosporin compounds in this specification are named with reference to "cepham" after *J. Amer. Chem. Soc.*, 1962, 84, 3400, the term "cephem" referring to the basic cepham structure with one double bond.

The compounds according to the invention are syn isomers. The syn isomeric form is defined by the configuration of the group

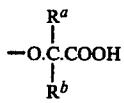

with respect to the carboxamido group. In this specification the syn configuration is denoted structurally as

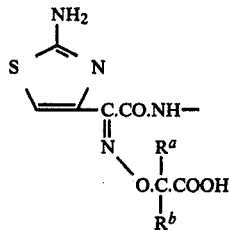

It will be understood that since the compounds according to the invention are capable of geometric isomerism, some admixture with the corresponding anti isomer may occur.

The invention also includes within its scope the solvates (especially the hydrates) of the compounds of formula (I). It also includes within its scope salts of esters of compounds of formula (I).

The compounds according to the present invention may exist in tautomeric forms (for example in respect of the 2-aminothiazolyl group) and it will be understood that such tautomeric forms, e.g. the 2-iminothiazolinyl form, are included within the scope of the invention. Moreover, the compounds of formula (I) depicted above may also exist in alternative zwitterionic forms, for example wherein the 4-carboxyl group is protonated and the terminal carboxyl group in the 7-side chain is deprotonated. Such zwitterionic forms and mixtures thereof are included within the scope of the present invention.

It will also be appreciated that when $R^a$ and $R^b$ in formula (I) represent different $C_{1-4}$ alkyl groups the carbon atom to which they are attached will comprise a centre of asymmetry. Such compounds are diasteroisomeric and the present invention embraces individual diasteroisomers of these compounds as well as mixtures thereof.

The compounds according to the invention exhibit broad spectrum antibiotic activity against a wide range of commonly encountered pathogenic organisms. Against gram-negative organisms the activity is unusually high. The high activity extends to many β-lactamase-producing gram-negative strains. The compounds also possess high stability to β-lactamases produced by a range of gram-positive and gram-negative organisms.

Compounds according to the invention have been found to exhibit unusually high activity against strains of Pseudomonas organisms, e.g. strains of *Pseudomonas aeruginosa* as well as high activity against various members of the Enterobacteriaceae (e.g. strains of *Escherichia coli, Klebsiella pneumoniae, Salmonella typhimurium, Shigella sonnei, Enterobacter cloacae, Serratia marcescens,* Providence species, *Proteus mirabilis* and especially indole positive Proteus organisms such as *Proteus vulgaris* and *Proteus morganii*), and strains of *Haemophilus influenzae.*

The antibiotic properties of the compounds according to the invention compare very favourably with those of the aminoglycosides such as amikacin or gentamicin. In particular, this applies to their activity against strains of various Pseudomonas organisms which are not susceptible to many existing commercially available antibiotic compounds. Unlike the aminoglycosides, cephalosporin antibiotics normally exhibit low toxicity in man. The use of aminoglycosides in human therapy tends to be limited or complicated by the relatively high toxicity of these antibiotics. The cephalosporin antibiotics of the present invention thus possess potentially great advantages over the aminoglycosides.

Non-toxic salt derivatives which may be formed from the compounds of general formula (I) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenethylbenzylamine, dibenzylethylenediamine, ethanolamine, diethanolamine and N-methylglucosamine salts). Other non-toxic salt derivatives include acid addition salts, e.g. formed with hydrochloric, hydrobromic, sulphuric, nitric, phosphoric, formic and trifluoroacetic acids. The salts may also be in the form of resinates formed with, for example, a polystyrene resin or cross-linked polystyrene divinylbenzene copolymer resin containing amino or quaternary amino groups or sulphonic acid groups, or with a resin containing carboxyl groups, e.g. a polyacrylic acid resin. Soluble base salts (e.g. alkali metal salts such as the sodium salt) of compounds of formula (I) may be used in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

These and other salt derivatives such as the salts with toluene-p-sulphonic and methanesulphonic acids may be employed as intermediates in the preparation and/or purification of the present compounds of formula (I), for example in the processes described below.

Non-toxic metabolically labile ester derivatives which may be formed from the parent compound of formula (I) include acyloxyalkyl esters, e.g. lower alkanoyloxy-methyl or -ethyl esters such as acetoxymethyl or -ethyl or pivaloyloxymethyl esters. In addition to the above ester derivatives, the present invention includes within its scope compounds of formula (I) in the form of other physiologically acceptable equivalents, i.e. physiologically acceptable compounds which, like the metabolically labile esters, are converted in vivo into the parent antibiotic compound of formula (I).

Preferred compounds according to the invention include those compounds of formula (I) wherein $R^a$ and $R^b$ both represent methyl groups or together with the carbon atom to which they are attached form a cyclobutylidene group. Further preferred compounds are those of formula (I) wherein $R^1$ represents a methyl group.

Particularly preferred compounds according to the present invention include (6R,7R)-7-[(Z)-2-(2-aminothiazol-4-yl)-2-(2-carboxyprop-2-oxyimino)acetamido]-3-(2-methylpyrazolium-1-ylmethyl)ceph-3-em-4-carboxylate and (6R,7R)-7-[(Z)-2-(2-aminothiazol-4-yl)-2-(1-carboxycylobut-1-oxyimino)acetamido]-3-(2-methylpyrazolium-1-ylmethyl)ceph-3-em-4-carboxylate, and their non-toxic salts and non-toxic metabolically labile esters.

Other compounds according to the present invention include those for example wherein the groups $R^a$, $R^b$ and $R^1$ are as follows:

|     | $R^a$ | $R^b$ | $R^1$ |
|-----|-------|-------|-------|
| (a) | Alkyl groups | | |
|     | —CH₃ | —C₂H₅ | —CH₃ |
|     | —C₂H₅ | —C₂H₅ | —CH₃ |
|     | —CH₃ | —CH₃ | —C₂H₅ |
|     | —CH₃ | —C₂H₅ | —C₂H₅ |
|     | —C₂H₅ | —C₂H₅ | —C₂H₅ |
| (b) | Cycloalkylidene groups | | |
|     | ($R^a$—C—$R^b$) | | |
|     | cyclopropylidene | | —CH₃ |
|     | cyclopentylidene | | —CH₃ |
|     | cyclopropylidene | | —C₂H₅ |
|     | cyclobutylidene | | —C₂H₅ |
|     | cyclopentylidene | | —C₂H₅ |

The above described compounds may be used for treating a variety of diseases caused by pathogenic bacteria in human beings and animals, such as respiratory tract infections and urinary tract infections.

According to a further embodiment of the present invention we provide a process for the preparation of compounds of formula (I) as hereinbefore defined or non-toxic salts or non-toxic metabolically labile esters thereof which comprises (A) acylating a compound of the formula

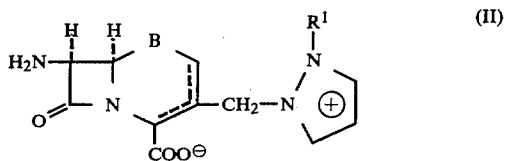

[wherein $R^1$ is as defined above, B is >S or >S→O (α- or β-), and the dotted line bridging the 2-, 3- and 4-positions indicates that the compound is a ceph-2-em or ceph-3-em compound], or an acid addition salt (formed with, for example, a mineral acid such as hydrochloric, hydrobromic, sulphuric, nitric or phosphoric acid or an organic acid such as methane-sulphonic or toluene-p-sulphonic acid) or an N-silyl derivative thereof, or a corresponding compound possessing a group of the formula —COOR²ᵃ at the 4-position where $R^{2a}$ is a hydrogen atom or a carboxyl blocking group e.g. the residue of an ester-forming aliphatic or araliphatic alcohol or an ester-forming phenol, silanol or stannanol (the said alcohol, phenol silanol or stannanol preferably containing 1 to 20 carbon atoms) and having an associated anion A⊖ such as a halide, e.g. chloride or bromide, or trifluoroacetate ion, with an acid of formula

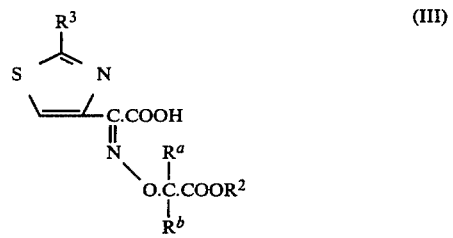

[wherein $R^a$ and $R^b$ are as hereinbefore defined; $R^2$ represents a carboxyl blocking group (e.g. as described for $R^{2a}$) and $R^3$ is an amino or protected amino group] or with an acylating agent corresponding thereto; (B) reacting a compound of formula

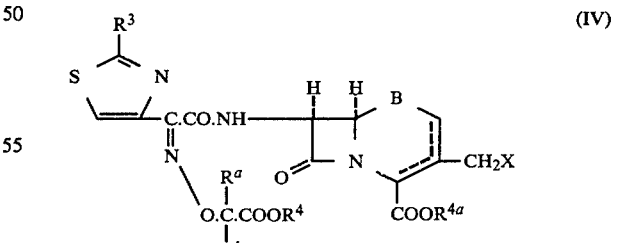

(wherein $R^a$, $R^b$, $R^3$, B and the dotted line are as hereinbefore defined; $R^4$ and $R^{4a}$ may independently represent hydrogen or a carboxyl blocking group; and X is a replaceable residue of a nucleophile, e.g. an acetoxy or dichloroacetoxy group or a halogen atom such as chlorine, bromine or iodine) or a salt thereof with an alkylpyrazole of the formula

 (V)

wherein $R^1$ is as defined above or (C) reacting a compound of the formula

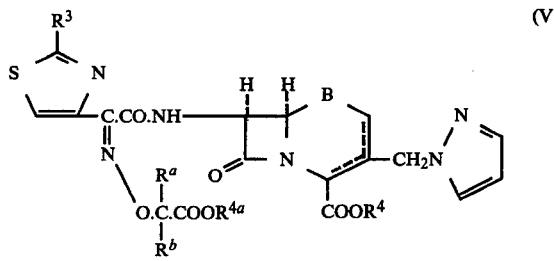 (VI)

(wherein $R^a$, $R^b$, $R^3$, B and the dotted line are as hereinbefore defined; and $R^4$ and $R^{4a}$ in this instance are both carboxyl blocking groups) with an alkylating agent serving to introduce the $R^1$ substituent onto the pyrazole nucleus; whereafter, if necessary and/or desired in each instance, any of the following reactions, in any appropriate sequence, are carried out:

(i) conversion of a $\Delta^2$-isomer into the desired $\Delta^3$-isomer, (ii) reduction of a compound wherein B is $>S\to O$ to form a compound wherein B is $>S$, (iii) conversion of a carboxyl group into a non-toxic salt or non-toxic metabolically labile ester function, and (iv) removal of any carboxyl blocking and/or N-protecting groups.

In the above-described process (A), the starting material of formula (II) is preferably a ceph-3-em compound.

Acylating agents which may be employed in the preparation of compounds of formula (I) include acid halides, particularly acid chlorides or bromides. Such acylating agents may be prepared by reacting an acid (III) or a salt thereof with a halogenating agent e.g. phosphorus pentachloride, thionyl chloride or oxalyl chloride.

Where an acid addition salt of the compound of formula (II) is used, this is generally treated with a base prior to reaction with the compound of formula (III) or an acylating agent corresponding thereto.

Acylations employing acid halides may be effected in aqueous and non-aqueous reaction media conveniently at temperatures of from $-50°$ to $+50°$ C. preferably $-20°$ to $+30°$ C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazole; or an isoxazolium salt such as N-ethyl-5-phenylisoxazolium perchlorate.

Acylation may also be effected with other amide-forming derivatives of acids of formula (III) such as, for example, an activated ester, a symmetrical anhydride or a mixed anhydride (e.g. formed with pivalic acid or with a haloformate such as a lower alkylhaloformate).

Mixed anhydrides may also be formed with phosphorus acids (for example, phosphoric or phosphorous acids), sulphuric acid or aliphatic or aromatic sulphonic acids (for example toluene-p-sulphonic acid).

An activated ester may conveniently be formed in situ using, for example, 1-hydroxybenzotriazole in the presence of a condensing agent as set out above. Alternatively, the activated ester may be preformed.

Acylation reactions involving the free acids or their above mentioned amide-forming derivatives are desirably effected in an anhydrous reaction medium e.g. methylene chloride, tetrahydrofuran, dimethylformamide or acetonitrile.

If desired, the above acylation reactions may be performed in the presence of a catalyst, e.g. 4-dimethylaminopyridine.

The amino acids of formula (III) and acylating agents corresponding thereto may, if desired, be prepared and employed in the form of their acid addition salts. Thus, for example, acid chlorides may conveniently be employed as their hydrochloride salts and acid bromides as their hydrobromide salts.

In process (B) above, the alkylpyrazole of formula (V) may displace a wide variety of substituents X from the cephalosporin of formula (IV). To some extent the facility of the displacement is related to the pKa of the acid HX from which the substituent is derived. Thus, atoms or groups X derived from strong acids tend, in general, to be more easily displaced than atoms or groups derived from weaker acids. The facility of the displacement may also be related, to some extent, to the identify of the substituent $R^1$ in the compound of formula (V).

The displacement of X in process (B) may conveniently be effected by maintaining the reactants in solution or suspension. The reaction is advantageously effected using from 1 to 30 moles e.g. 1 to 15 moles of the compound of formula (V) in a suitable reaction medium. Alternatively the compound (V) itself may be used as a solvent.

Nucleophilic displacement reactions may conveniently be carried out on those compounds of formula (IV) wherein the substituent X is a halogen atom or an acyloxy group, for example as discussed below.

ACYLOXY GROUPS

Compounds of formula (IV) wherein X is an acetoxy group are convenient starting materials for use in the nucleophilic displacement reaction with the compound of formula (V). Alternative starting materials in this class include compounds of formula (IV) in which X is the residue of a substituted acetic acid e.g. chloroacetic acid, dichloroacetic acid and trifluoroacetic acid.

Displacement reactions on compounds (IV) possessing X substituents of this class, particularly in the case where X is an acetoxy group, may be facilitated by the presence in the reaction medium of iodide or thiocyanate ions.

The substituent X may also be derived from formic acid, a haloformic acid such as chloroformic acid, or a carbamic acid.

When using a compound of formula (IV) in which X represents an acetoxy or substituted acetoxy group, it is generally desirable that the group $R^4$ in formula (IV) should be a hydrogen atom and that B should represent $>S$. In this case, the reaction is advantageously effected in an aqueous medium.

Under aqueous conditions, the pH value of the reaction solution is advantageously maintained in the range 6-8, if necessary by the addition of a base. The base is conveniently an alkali metal or alkaline earth metal hydroxide or bicarbonate such as sodium hydroxide or sodium bicarbonate.

When using compounds of formula (IV) in which X is an acetoxy group, the reaction is conveniently effected at a temperature of 30° C. to 110° C., preferably 50° C. to 90° C.

The above described process employing compounds of formula (IV) in which X is the residue of a substituted acetic acid may be carried out as described in British Patent Specification No. 1,241,657

HALOGENS

Compounds of formula (IV) in which X is a chlorine, bromine or iodine atom can also be conveniently used as starting materials in the nucleophilic displacement reaction with the compound of formula (V). When using compounds of formula (IV) in this class, B may represent $>S\rightarrow O$ and $R^4$ may represent a carboxyl blocking group. The reaction is conveniently effected in a non-aqueous medium which preferably comprises one or more organic solvents, advantageously of a polar nature such as ethers, e.g. dioxan or tetrahydrofuran, esters, e.g. ethyl acetate, amides, e.g. formamide or N,N-dimethylformamide or ketones e.g. acetone. Other suitable organic solvents are described in more detail in British Patent Specification No. 1,326,531.

In the case of reactions carried out on compounds of formula (IV) in which $R^4$ and $R^{4a}$ are carboxyl blocking groups the product will be formed as the corresponding halide salt which may, if desired, be subjected to one or more ion exchange reactions to obtain a salt having the desired anion.

When using compounds of formula (IV) in which X is a halogen atom as described above, the reaction is conveniently effected at a temperature of −20° to +60°, preferably 0° to +30° C.

In process (C) above, the compound of formula (VI) is advantageously reacted with an alkylating agent of the formula $R^1Y$ where Y is a leaving group such as a halogen atom (e.g. iodine, chlorine or bromine) or a hydrocarbyl sulphonate (e.g. mesylate or tosylate) group, or $R^1Y$ may represent a dialkyl sulphate e.g. dimethylsulphate. Iodomethane is preferred as a methylating agent. The alkylation reaction is preferably carried out at a temperature in the range of 0° to 60° C., advantageously 20° to 40° C. Where the alkylating agent is liquid under the reaction conditions, as in the case of iodomethane, this can itself serve as a solvent. Alternatively the reaction may conveniently be effected in an inert solvent such as an ether e.g. tetrahydrofuran, an amide, e.g. dimethylformamide, a lower alkanol e.g. ethanol, a lower dialkylketone, e.g. acetone, a halogenated hydrocarbon e.g. dichloromethane or chloroform, or an ester, e.g. ethyl acetate.

The compound of formula (VI) used as starting material in process (C) may be prepared for example by reaction of a compound of formula (IV) (as defined above) with pyrazole in an analogous manner to the nucleophilic displacement reaction described with respect to process (B).

The reaction product may be separated from the reaction mixture, which may contain, for example, unreacted nucleophile and other substances, by a variety of processes including recrystallisation, ionophoresis, column chromatography and use of ion-exchangers (for example by chromatography on ion-exchange resins) or macroreticular resins.

A $\Delta^2$-cephalosporin ester derivative obtained in accordance with the process of the invention may be converted into the corresponding $\Delta^3$-derivative by, for example, treatment of the $\Delta^2$-ester with a base such as pyridine or triethylamine.

A ceph-2-em reaction product may also be oxidised to yield the corresponding ceph-3-em 1-oxide, for example by reaction with a peracid e.g. peracetic or m-chloroperbenzoic acid; the resulting sulphoxide may, if desired, subsequently be reduced as described hereinafter to yield the corresponding ceph-3-em sulphide.

Where a compound is obtained in which B is $>S\rightarrow O$ this may be converted to the corresponding sulphide by, for example, reduction of the corresponding acyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, acetone, tetrahydrofuran, dioxan, dimethylformamide or dimethylacetamide. The reaction may be effected at a temperature between −20° to +50° C.

Metabolically labile ester derivatives of the compounds of formula (I) may be prepared by reacting a compound of formula (I) or a salt or protected derivative thereof with the appropriate esterifying agent such as an acyloxymethyl halide (e.g. iodide), conveniently in an inert organic solvent such as dimethylformamide or acetone, followed, where necessary, by removal of any protecting groups.

Base salts of the compounds of formula (I) may be formed by reacting an acid of formula (I) with an appropriate base. Thus, for example, sodium or potassium salts may be prepared using the respective 2-ethyl hexanoate or hydrogen carbonate salts. Acid addition salts may be prepared by reacting a compound of formula (I) or a metabolically labile ester derivative thereof with the appropriate acid.

Where a compound of formula (I) is obtained as a mixture of isomers, the syn isomer may be obtained by, for example, conventional methods such as crystallisation or chromatography.

For use as starting materials for the preparation of the compounds of formula (I) according to the invention, compounds of general formula (III) and acid halides and anhydrides corresponding thereto in their syn isomeric form, or in the form of mixtures of the syn isomers and the corresponding anti isomers containing at least 90% of the syn isomer, are preferably used.

Acids of formula (III) (provided that $R^a$ and $R^b$ together with the carbon atom to which they are attached do not form a cyclopropylidene group) may be prepared by etherification of a compound of formula presence in the reaction medium of iodide or thiocyanate ions.

The substituent X may also be derived from formic acid, a haloformic acid such as chloroformic acid, or a carbamic acid.

When using a compound of formula (IV) in which X represents an acetoxy or substituted acetoxy group, it is generally desirable that the group $R^4$ in formula (IV) should be a hydrogen atom and that B should represent $>S$. In this case, the reaction is advantageously effected in an aqueous medium.

Under aqueous conditions, the pH value of the reaction solution is advantageously maintained in the range 6–8, if necessary by the addition of a base. The base is conveniently an alkali metal or alkaline earth metal hydroxide or bicarbonate such as sodium hydroxide or sodium bicarbonate.

When using compounds of formula (IV) in which X is an acetoxy group, the reaction is conveniently effected at a temperature of 30° C. to 110° C., preferably 50° C. to 90° C.

The above described process employing compounds of formula (IV) in which X is the residue of a substituted acetic acid may be carried out as described in British Patent Specification No. 1,241,657

HALOGENS

Compounds of formula (IV) in which X is a chlorine, bromine or iodine atom can also be conveniently used as starting materials in the nucleophilic displacement reaction with the compound of formula (V). When using compounds of formula (IV) in this class, B may represent $>S\rightarrow O$ and $R^4$ may represent a carboxyl blocking group. The reaction is conveniently effected in a non-aqueous medium which preferably comprises one or more organic solvents, advantageously of a polar nature such as ethers, e.g. dioxan or tetrahydrofuran, esters, e.g. ethyl acetate, amides, e.g. formamide or N,N-dimethylformamide or ketones e.g. acetone. Other suitable organic solvents are described in more detail in British Patent Specification No. 1,326,531.

In the case of reactions carried out on compounds of formula (IV) in which $R^4$ and $R^{4a}$ are carboxyl blocking groups the product will be formed as the corresponding halide salt which may, if desired, be subjected to one or more ion exchange reactions to obtain a salt having the desired anion.

When using compounds of formula (IV) in which X is a halogen atom as described above, the reaction is conveniently effected at a temperature of $-20°$ to $+60°$, preferably 0° to $+30°$ C.

In process (C) above, the compound of formula (VI) is advantageously reacted with an alkylating agent of the formula $R^1Y$ where Y is a leaving group such as a halogen atom (e.g. iodine, chlorine or bromine) or a hydrocarbyl sulphonate (e.g. mesylate or tosylate) group, or $R^1Y$ may represent a dialkyl sulphate e.g. dimethylsulphate. Iodomethane is preferred as a methylating agent. The alkylation reaction is preferably carried out at a temperature in the range of 0° to 60° C., advantageously 20° to 40° C. Where the alkylating agent is liquid under the reaction conditions, as in the case of iodomethane, this can itself serve as a solvent. Alternatively the reaction may conveniently be effected in an inert solvent such as an ether e.g. tetrahydrofuran, an amide, e.g. dimethylformamide, a lower alkanol e.g. ethanol, a lower dialkylketone, e.g. acetone, a halogenated hydrocarbon e.g. dichloromethane or chloroform, or an ester, e.g. ethyl acetate.

The compound of formula (VI) used as starting material in process (C) may be prepared for example by reaction of a compound of formula (IV) (as defined above) with pyrazole in an analogous manner to the nucleophilic displacement reaction described with respect to process (B).

The reaction product may be separated from the reaction mixture, which may contain, for example, unreacted nucleophile and other substances, by a variety of processes including recrystallisation, ionophoresis, column chromatography and use of ion-exchangers (for example by chromatography on ion-exchange resins) or macroreticular resins.

A $\Delta^2$-cephalosporin ester derivative obtained in accordance with the process of the invention may be converted into the corresponding $\Delta^3$-derivative by, for example, treatment of the $\Delta^2$-ester with a base such as pyridine or triethylamine.

A ceph-2-em reaction product may also be oxidised to yield the corresponding ceph-3-em 1-oxide, for example by reaction with a peracid e.g. peracetic or m-chloroperbenzoic acid; the resulting sulphoxide may, if desired, subsequently be reduced as described hereinafter to yield the corresponding ceph-3-em sulphide.

Where a compound is obtained in which B is $>S\rightarrow O$ this may be converted to the corresponding sulphide by, for example, reduction of the corresponding acyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, acetone, tetrahydrofuran, dioxan, dimethylformamide or dimethylacetamide. The reaction may be effected at a temperature between $-20°$ to $+50°$ C.

Metabolically labile ester derivatives of the compounds of formula (I) may be prepared by reacting a compound of formula (I) or a salt or protected derivative thereof with the appropriate esterifying agent such as an acyloxymethyl halide (e.g. iodide), conveniently in an inert organic solvent such as dimethylformamide or acetone, followed, where necessary, by removal of any protecting groups.

Base salts of the compounds of formula (I) may be formed by reacting an acid of formula (I) with an appropriate base. Thus, for example, sodium or potassium salts may be prepared using the respective 2-ethyl hexanoate or hydrogen carbonate salts. Acid addition salts may be prepared by reacting a compound of formula (I) or a metabolically labile ester derivative thereof with the appropriate acid.

Where a compound of formula (I) is obtained as a mixture of isomers, the syn isomer may be obtained by, for example, conventional methods such as crystallisation or chromatography.

For use as starting materials for the preparation of the compounds of formula (I) according to the invention, compounds of general formula (III) and acid halides and anhydrides corresponding thereto in their syn isomeric form, or in the form of mixtures of the syn isomers and the corresponding anti isomers containing at least 90% of the syn isomer, are preferably used.

Acids of formula (III) (provided that $R^a$ and $R^b$ together with the carbon atom to which they are attached do not form a cyclopropylidene group) may be prepared by etherification of a compound of formula

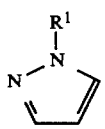

wherein R¹ is as defined above or (C) reacting a compound of the formula

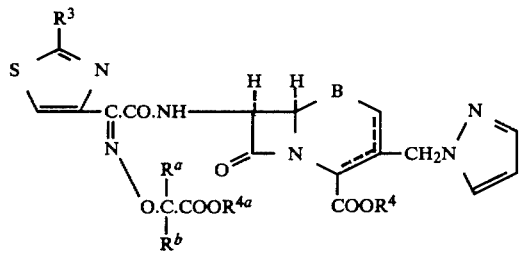

(wherein $R^a$, $R^b$, $R^3$, B and the dotted line are as hereinbefore defined; and $R^4$ and $R^{4a}$ in this instance are both carboxyl blocking groups) with an alkylating agent serving to introduce the $R^1$ substituent onto the pyrazole nucleus; whereafter, if necessary and/or desired in each instance, any of the following reactions, in any appropriate sequence, are carried out:

(i) conversion of a $\Delta^2$-isomer into the desired $\Delta^3$-isomer, (ii) reduction of a compound wherein B is $>S \to O$ to form a compound wherein B is $>S$, (iii) conversion of a carboxyl group into a non-toxic salt or non-toxic metabolically labile ester function, and (iv) removal of any carboxyl blocking and/or N-protecting groups.

In the above-described process (A), the starting material of formula (II) is preferably a ceph-3-em compound.

Acylating agents which may be employed in the preparation of compounds of formula (I) include acid halides, particularly acid chlorides or bromides. Such acylating agents may be prepared by reacting an acid (III) or a salt thereof with a halogenating agent e.g. phosphorus pentachloride, thionyl chloride or oxalyl chloride.

Where an acid addition salt of the compound of formula (II) is used, this is generally treated with a base prior to reaction with the compound of formula (III) or an acylating agent corresponding thereto.

Acylations employing acid halides may be effected in aqueous and non-aqueous reaction media conveniently at temperatures of from $-50°$ to $+50°$ C. preferably $-20°$ to $+30°$ C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazole; or an isoxazolium salt such as N-ethyl-5-phenylisoxazolium perchlorate.

Acylation may also be effected with other amide-forming derivatives of acids of formula (III) such as, for example, an activated ester, a symmetrical anhydride or a mixed anhydride (e.g. formed with pivalic acid or with a haloformate such as a lower alkylhaloformate).

Mixed anhydrides may also be formed with phosphorus acids (for example, phosphoric or phosphorous acids), sulphuric acid or aliphatic or aromatic sulphonic acids (for example toluene-p-sulphonic acid).

An activated ester may conveniently be formed in situ using, for example, 1-hydroxybenzotriazole in the presence of a condensing agent as set out above. Alternatively, the activated ester may be preformed.

Acylation reactions involving the free acids or their above mentioned amide-forming derivatives are desirably effected in an anhydrous reaction medium e.g. methylene chloride, tetrahydrofuran, dimethylformamide or acetonitrile.

If desired, the above acylation reactions may be performed in the presence of a catalyst, e.g. 4-dimethylaminopyridine.

The amino acids of formula (III) and acylating agents corresponding thereto may, if desired, be prepared and employed in the form of their acid addition salts. Thus, for example, acid chlorides may conveniently be employed as their hydrochloride salts and acid bromides as their hydrobromide salts.

In process (B) above, the alkylpyrazole of formula (V) may displace a wide variety of substituents X from the cephalosporin of formula (IV). To some extent the facility of the displacement is related to the pKa of the acid HX from which the substituent is derived. Thus, atoms or groups X derived from strong acids tend, in general, to be more easily displaced than atoms or groups derived from weaker acids. The facility of the displacement may also be related, to some extent, to the identify of the substituent $R^1$ in the compound of formula (V).

The displacement of X in process (B) may conveniently be effected by maintaining the reactants in solution or suspension. The reaction is advantageously effected using from 1 to 30 moles e.g. 1 to 15 moles of the compound of formula (V) in a suitable reaction medium. Alternatively the compound (V) itself may be used as a solvent.

Nucleophilic displacement reactions may conveniently be carried out on those compounds of formula (IV) wherein the substituent X is a halogen atom or an acyloxy group, for example as discussed below.

ACYLOXY GROUPS

Compounds of formula (IV) wherein X is an acetoxy group are convenient starting materials for use in the nucleophilic displacement reaction with the compound of formula (V). Alternative starting materials in this class include compounds of formula (IV) in which X is the residue of a substituted acetic acid e.g. chloroacetic acid, dichloroacetic acid and trifluoroacetic acid.

Displacement reactions on compounds (IV) possessing X substituents of this class, particularly in the case where X is an acetoxy group, may be facilitated by the

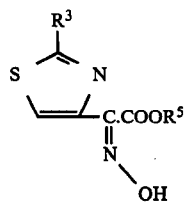

(VII)

(wherein R³ is as hereinbefore defined and R⁵ represents a carboxyl blocking group) by reaction with a compound of general formula

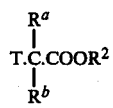

(VIII)

(wherein $R^a$, $R^b$, and $R^2$ are as hereinbefore defined and T is halogen such as chloro, bromo, or iodo; sulphate; or sulphonate such as tosylate) followed by removal of the carboxyl blocking group $R^5$. Separation of isomers may be effected either before or after such etherification. The etherification reaction is generally carried out in the presence of a base, e.g. potassium carbonate or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oxyimino group is substantially unchanged by the etherification reaction.

The reaction should be effected in the presence of a base if an acid addition salt of a compound of formula (VII) is used. The base should be used in sufficient quantity so as rapidly to neutralise the acid in question.

Acids of general formula (III) may also be prepared by reaction of a compound of formula

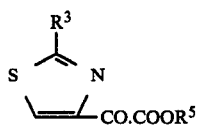

(IX)

(wherein $R^3$ and $R^5$ are as hereinbefore defined) with a compound of formula

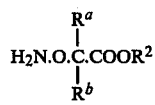

(X)

(wherein $R^a$, $R^b$ and $R^2$ are as defined above), followed by removal of the carboxyl blocking group $R^5$, and where necessary by separation of syn and anti isomers.

The last mentioned reaction is particularly applicable to the preparation of acids of formula (III) wherein $R^a$ and $R^b$ together with the carbon atom to which they are attached form a cyclopropylidene group. In this case, the relevant compounds of formula (X) may be prepared in conventional manner, e.g. by means of the synthesis described in Belgian Patent Specification No. 866 422 for the preparation of t-butyl 1-amino-oxycyclopropane carboxylate.

The acids of formula (III) may be converted to the corresponding acid halides and anhydrides and acid addition salts by conventional methods for example as described hereinabove.

Where X is a halogen (i.e. chlorine, bromine or iodine) atom in formula (IV), ceph-3-em starting compounds may be prepared in conventional manner, e.g. by halogenation of a 7β-protected amino-3-methylceph-3-em-4-carboxylic acid ester 1β-oxide, removal of the 7β-protecting group, acylation of the resulting 7β-amino compound to form the desired 7β-acylamido group, e.g. in an analogous manner to process (A) above, followed by reduction of the 1β-oxide group later in the sequence. This is described in British Pat. No. 1,326,531. The corresponding ceph-2-em compounds may be prepared by the method of Dutch published Patent Application No. 6,902,013 for example by reaction of a 3-methylceph-2-em compound with N-bromosuccinimide to yield the corresponding 3-bromomethylceph-2-em compound.

Where X in formula (IV) is an acetoxy group, such starting materials may be prepared for example by acylation of 7-aminocephalosporanic acid, e.g. in an analogous manner to process (A) above. Compounds of formula (IV) in which X represents other acyloxy groups can be prepared by acylation of the corresponding 3-hydroxymethyl compounds which may be prepared for example by hydrolysis of the appropriate 3-acetoxymethyl compounds e.g. as described inter alia in British Patent Specification Nos. 1,474,519 and 1,531,212.

Compounds of formula (II) may likewise be prepared in conventional manner, e.g. by nucleophilic displacement of a corresponding 3-acyloxymethyl or 3-halomethyl compound with an alkylpyrazole.

A further method for the preparation of starting materials of formula (II) comprises deprotecting the corresponding protected 7β-amino compound in conventional manner, e.g. using $PCl_5$.

It is to be noted that compounds of formula (II) are novel and constitute a further aspect of the present invention.

It should be appreciated that in some of the above transformations it may be necessary to protect any sensitive groups in the molecule of the compound in question to avoid undesirable side-reactions. For example, during any of the reaction sequences referred to above it may be necessary to protect the $NH_2$ group of the aminothiazolyl moiety, for example by tritylation, acylation (e.g. chloracetylation), protonation or other conventional method. The protecting group may thereafter be removed in any convenient way which does not cause breakdown of the desired compound, e.g. in the case of trityl group by using an optionally halogenated carboxylic acid such as acetic acid, formic acid, chloroacetic acid or trifluoroacetic acid or using a mineral acid, e.g. hydrochloric acid or mixtures of such acids, conveniently in the presence of a protic solvent such as water or, in the case of a chloroacetyl group, by treatment with thiourea.

Carboxyl blocking groups used in the preparation of the compounds of formula (I) or in the preparation of necessary starting materials are desirably groups which may readily be split off at a suitable stage in the reaction sequence, conveniently at the last stage. It may, however, be convenient in some instances to employ biologically acceptable, metabolically labile carboxyl blocking groups such as acyloxy-methyl or -ethyl groups (e.g. acetoxy-methyl or -ethyl and pivaloyloxymethyl groups) and retain these in the final product to give a biologically acceptable ester derivative of the compound of formula (I).

Suitable carboxyl blocking groups are well known in the art, a list of representative blocked carboxyl groups being included in British Pat. No. 1,399,086. Preferred blocked carboxyl groups include aryl lower alkoxycarbonyl groups such as p-methoxybenzyloxycarbonyl, p-nitrobenzyloxycarbonyl and diphenylmethoxycarbonyl; t-butoxycarbonyl; and lower haloalkoxycarbonyl groups such as 2,2,2-trichloroethoxycarbonyl. Carboxyl blocking group(s) may subsequently be removed by any of the appropriate methods disclosed in the literature; thus, for example, acid or base catalysed hydrolysis is applicable in many cases, as are enzymically-catalysed hydrolyses.

The following Examples illustrate the invention. All temperatures are in °C. "Petrol" means petroleum ether (b.p. 40°-60° C.). "Ether" refers to diethyl ether and Calofort "U" is a form of finely divided calcium carbonate. T.l.c. refers to thin-layer chromatography. Proton magnetic resonance spectra were determined on the products at 100 MHz. The integrals were in agreement with the assignments; the signs of the coupling constants, J, in Hz, were not determined. The following abbreviations are used: s=singlet, d=doublet, dd=double doublet, m=multiplet and ABq=AB-quartet.

PREPARATION 1

Ethyl (Z)-2-(2-aminothiazol-4-yl)-2-(hydroxyimino) acetate

To a stirred and ice-cooled solution of ethyl acetoacetate (292 g) in glacial acetic acid (296 ml) was added a solution of sodium nitrite (180 g) in water (400 ml) at such a rate that the reaction temperature was maintained below 10° C. Stirring and cooling were continued for about 30 min, when a solution of potassium chloride (160 g) in water (800 ml) was added. The resulting mixture was stirred for one hour. The lower oily phase was separated and the aqueous phase was extracted with diethyl ether. The extract was combined with the oil, washed successively with water and saturated brine, dried, and evaporated. The residual oil, which solidified on standing, was washed with petrol and dried in vacuo over potassium hydroxide, giving ethyl (Z)-2-(hydroxyimino)-3-oxobutyrate (309 g).

A stirred and ice-cooled solution of ethyl (Z)-2-(hydroxyimino)-3-oxobutyrate (150 g) in dichloromethane (400 ml) was treated dropwise with sulphuryl chloride (140 g). The resulting solution was kept at room temperature for 3 days, then evaporated. The residue was dissolved in diethyl ether, washed with water until the washings were almost neutral, dried, and evaporated. The residual oil (177 g) was dissolved in ethanol (500 ml) and dimethylaniline (77 ml) and thiourea (42 g) was added with stirring. After two hours, the mixture was filtered and the residue washed with ethanol and dried to give the title compound (73 g); m.p. 188° (decomp).

PREPARATION 2

Ethyl (Z)-2-hydroxyimino-2-(2-tritylaminothiazol-4-yl)-acetate, hydrochloride Trityl chloride (16.75 g) was added portionwise over 2 hours to a stirred and cooled (−30°) solution of the product of Preparation 1 (12.91 g) and triethylamine (8.4 ml) in dimethylformamide (28 ml). The mixture was allowed to warm to 15° over one hour, stirred for a further 2 hours and then partitioned between water (500 ml) and ethyl acetate (500 ml). The organic phase was separated, washed with water (2×500 ml) and then shaken with 1N HCl (500 ml). The precipitate was collected, washed successively with water (100 ml), ethyl acetate (200 ml) and ether (200 ml) and dried in vacuo to provide the title compound as a white solid (16.4 g); m.p. 184° to 186° (decomp).

PREPARATION 3

Ethyl (Z)-2-(2-t-butoxycarbonylprop-2-oxyimino)-2-(2-tritylaminothiazol-4-yl)acetate Potassium carbonate (34.6 g) and t-butyl 2-bromo-2-methylpropionate (24.5 g) were added to a stirred solution under nitrogen of the product of Preparation 2 (49.4 g) in dimethylsulphoxide (200 ml) and the mixture was stirred at room temperature for 6 hours. The mixture was poured into water (2 l), stirred for 10 min, and filtered. The solid was washed with water and dissolved in ethyl acetate (600 ml). The solution was washed successively with water, 2N hydrochloric acid, water, and saturated brine, dried and evaporated. The residue was recrystallised from petrol to give the title compound (34 g), m.p. 123.5° to 125°.

PREPARATION 4

(Z)-2-(2-t-Butoxycarbonylprop-2-oxyimino)-2-(2-tritylaminothiazol-4-yl)acetic acid The product of Preparation 3 (2 g) was dissolved in methanol (20 ml) and 2N sodium hydroxide (3.3 ml) was added. The mixture was refluxed for 1.5 hours and then concentrated. The residue was taken up in a mixture of water (50 ml), 2N hydrochloric acid (7 ml), and ethyl acetate (50 ml). The organic phase was separated, and the aqueous phase extracted with ethyl acetate. The organic solutions were combined, washed successively with water and saturated brine, dried, and evaporated. The residue was recrystallised from a mixture of carbon tetrachloride and petrol to give the title compound (1 g), m.p. 152° to 156° (decomp).

PREPARATION 5

Ethyl (Z)-2-(2-tritylaminothiazol-4-yl)-2-(1-t-butoxycarbonyl-cyclobut-1-oxyimino)acetate The product of Preparation 2 (55.8 g) was stirred under nitrogen in dimethylsulphoxide (400 ml) with potassium carbonate (finely ground, 31.2 g) at room temperature. After 30 minutes, t-butyl 1-bromocyclobutane carboxylate (29.2 g) was added. After 8 hours further potassium carbonate (31.2 g) was added. More potassium carbonate (6×16 g portions) was added during the next three days and further t-butyl 1-bromocyclobutane carboxylate (3.45 g) was added after 3 days. After 4 days in all, the mixture was poured into ice-water (ca. 3 liters) and the solid was collected by filtration and washed well with water and petrol. The solid was dissolved in ethyl acetate and the solution washed with brine (twice), dried with magnesium sulphate and evaporated to a foam. This foam was dissolved in ethyl acetate-petrol (1:2) and filtered through silica gel (500 g). Evaporation give the title compound (60 g) as a yellow foam, $\nu_{max}$ (CHBr$_3$) 3400 (NH) and 1730 cm$^{-1}$ (ester).

PREPARATION 6

(Z)-2-(1-t-Butoxycarbonylcyclobut-1-oxyimino)-2-(2-tritylaminothiazol-4-yl) acetic acid A mixture of the product of Preparation 5 (3.2 g) and potassium carbonate (1.65 g) was refluxed in methanol (180 ml) and water (20 ml) for 9 hours and the mixture was cooled to room temperature. The mixture was concentrated and the residue partitioned between ethyl acetate and water, to which was added 2N HCl (12.2 ml). The organic phase was separated and the aqueous phase extracted with ethyl acetate. The combined organic extracts were washed with saturated brine, dried and evaporated to give the title compound (2.3 g); $\lambda_{max}$ (ethanol) 265 nm ($E_{1\ cm}^{1\%}$ 243).

EXAMPLE 1

(a) Diphenylmethyl (1S,6R,7R)-3-Bromomethyl-7-[(Z)-2-(2-t-butoxycarbonylprop-2-oxyimino)-2-(2-tritylaminothiazol-4-yl)acetamido]ceph-3-em-4-carboxylate, 1-Oxide A solution of the product of Preparation 4 (0.526 g) in dry tetrahydrofuran (6 ml) was treated sucessively with 1-hydroxybenztriazole monohydrate (0.141 g) and N,N'-dicyclohexylcarbodiimide (0.198 g) in tetrahydrofuran (4 ml). The developing suspension was stirred for 30 minutes at 23° and then filtered. A solution of diphenylmethyl (1S,6R,7R)-7-amino-3-bromomethylceph-3-em-4-carboxylate, 1-oxide (0.427 g) in dichloromethane (260 ml) was treated at 23° with the above filtrate. The solution was stirred for 18 hours at 20° to 25°, evaporated to dryness, then the residue was dissolved in dichloromethane and washed successively with saturated aqueous sodium bicarbonate, water and brine, then dried and evaporated in vacuo to a foam (1.01 g).

This foam was purified by chromatography on preparative silica plates using toluene:ethyl acetate:acetic acid=190:50:2.5 as eluant. The purified product was isolated as a foam which was dissolved in ethyl acetate (5 ml) and precipitated from petrol (200 ml) to give the title compound (0.69 g) as a colourless powder; $\lambda_{max}$ (EtOH) 268 nm ($E_{1\ cm}^{1\%}$ 182) with an inflection at 242 nm ($E_{1\ cm}^{1\%}$ 230), $\nu_{max}$ (Nujol) 3375 (NH), 1805 ($\beta$-lactam), 1730 (CO$_2$R) and 1688 and 1515 cm$^{-1}$ (CONH).

(b) Diphenylmethyl (1S,6R,7R)-7-[(Z)-2-(2-t-Butoxycarbonylprop-2-oxyimino)-2-(2-tritylaminothiazol-4-yl)acetamido]-3-(2-methylpyrazolium-1-ylmethyl)ceph-3-em-4-carboxylate, 1-Oxide Bromide Salt A mixture of the product of stage (a) (0.95 g) and 1-methylpyrazole (1.3 g) were stirred in tetrahydrofuran (15 ml) at 22° in the absence of light for 4 days.

Another portion of 1-methylpyrazole (0.4 g) was added and stirring was continued for a further 5 days. The solution was evaporated to dryness and the residue was treated with ether:ethyl acetate (20:1) to give the title compound (0.91 g); $\tau$(DMSO-d$_6$) 1.24 (s, Ph$_3$CNH), 1.50 (m, pyrazolium 3—H) 1.68 (m, pyrazolium 5—H), 3.20 (s, thiazol-5-yl proton), 4.83 (d, J 5 Hz, 6—H), 6.14 (s, NMe$^\oplus$)

(c) Diphenylmethyl (6R,7R)-7-[(Z)-2-(2-t-Butoxycarbonylprop-2-oxyimino)-2-(2-tritylaminothiazol-4-yl)acetamido]-3-(2-methylpyrazolium-1-ylmethyl)ceph-3-em-4-Carboxylate, Iodide Salt A cooled ($-10°$) solution of the product of Stage (b) (0.85 g) in acetone (16 ml) was treated with potassium iodide (0.537 g) and stirred for 10 minutes.

A further portion of potassium iodide (0.537 g) was added followed by acetyl chloride (0.13 ml) and the suspension was stirred for 30 minutes at $-10°$ to $-2°$. The mixture was poured into a solution of sodium metabisulphite (0.4 g) in water (60 ml) and brine (30 ml). The product was extracted into dichloromethane and the organic extracts were washed with brine, dried and evaporated to a foam.

The reduction sequence using potassium iodide and acetyl chloride was repeated twice to give the title compound (0.57 g) as a foam; $\tau$(DMSO-d$_6$) 0.90 (s, Ph$_3$CNH) 1.48 (d, J 3 Hz, pyrazolium 3—H), 1.58 (d, J 3 Hz, pyrazolium 5—H), 3.27 (s, thiazol-5-yl proton), 4.74 (d, J 5 Hz, 6—H), 6.16 (s, NMe$^\oplus$).

(d) (6R,7R)-7-[(Z)-2-(2-Aminothiazol-4-yl)-2-(2-Carboxyprop-2-oxyimino)acetamido]-3-(2-methylpyrazolium-1-ylmethyl)ceph-3-em-4-carboxylate The product of stage (c) (0.5 g) in anisole (0.5 ml) and trifluoroacetic acid (2 ml) was allowed to stand for 1 minute and then the mixture was evaporated in vacuo to give an oil which, on treatment with ether gave a powder.

A suspension of this powder in anisole (0.5 ml) and trifluoroacetic acid (10 ml) was stirred for 15 minutes and filtered through a sinter. The filtrate was evaporated in vacuo to give an oil which, on trituration with ether afforded a powder (0.29 g).

This powder (0.29 g) was stirred with water (100 ml) and trifluoroacetic acid (5 ml) for 15 minutes, washed with ethyl acetate and ether and freeze-dried to give a solid which was dried in vacuo over phosphorus pentoxide to give the title compound, associated with 2 moles trifluoroacetic acid (0.23 g); $[\alpha]_D^{24}+6.6°$ (c 0.71, DMSO), $\lambda_{max}$ (pH6 phosphate) 226.5 nm ($E_{1\ cm}^{1\%}$ 299, $\epsilon$ 24,060) with $\lambda_{inf}$ at 253 nm ($E_{1\ cm}^{1\%}$ 243, $\epsilon$ 19,550) and 295 nm ($E_1$ cm$^{1\%}$ 106, $\epsilon$ 8,530).

EXAMPLE 2

(a) Diphenylmethyl (1S,6R,7R)-3-Bromomethyl-7-[(Z)-2-(1-t-butoxycarbonylcyclobut-1-oxyimino)-2-(2-tritylaminothiazol-4-yl)acetamido]ceph-3-em-4-carboxylate, 1-Oxide A stirred solution of the product of Preparation 6 (1.167 g) in tetrahydrofuran (15 ml) was treated successively with 1-hydroxybenztriazole hydrate (0.337 g) and N,N'-dicyclohexylcarbodiimide (0.495 g) for 30 minutes at 22°.

Filtration afforded a solution of the activated ester which was added to a solution of diphenylmethyl (1S,6R,7R)-7-amino-bromomethylceph-3-em-4-carboxylate 1-oxide (0.95 g) in dichloromethane (550 ml). The solution was stirred for 16 hours then evaporated to dryness. A solution of the residue in dichloromethane was washed successively with aqueous sodium bicarbonate, and brine, and then dried and evaporated to a foam (2.2 g) which was purified by preparative thin-layer chromatography (using toluene:ethyl acetate:acetic acid=40:10:1 for development) to give the title compound (1.4 g) with $\lambda_{max}$ (EtOH) 266 nm (E$_1$ cm$^{1\%}$ 192) and an inflection at 242.5 nm (E$_1$ cm$^{1\%}$ 224), $\nu_{max}$(Nujol) 3360 (NH), 1805 ($\beta$-lactam), 1730 (CO$_2$R) and 1689 and 1520 cm$^{-1}$ (CONH).

(b) Diphenylmethyl (1S,6R,7R)-7-[(Z)-2-(1-t-Butoxycarbonylcyclobut-1-oxyimino)-2-(2-tritylaminothiazol-4-yl)acetamido]-3-(2-methylpyrazolium-1-ylmethyl)ceph-3-em-4-carboxylate, 1-oxide, Bromide salt A mixture of the product of stage (a) (1.3 g) in tetrahydrofuran (20 ml) was treated with 1-methylpyrazole (2.6 g) and the mixture was stirred for 8 days at 20° to 25°.

The solution was evaporated to an oil which, on treatment with ether gave a powder. This powder was stirred with ethyl acetate to give the title compound (0.5 g) as a solid.

The organic liquors were evaporated and stirred with ethyl acetate:ether (1:1) to give a further crop of title compound (0.15 g) with $\tau$(DMSO-d$_6$) 1.00 (s, Ph$_3$CNH), 1.30 (d, J 9 Hz, CONH), 1.42 (m, pyrazolium 3—H), 1.62 (m, pyrazolium 5—H), 3.13 (s, thiazol 5—H), 3.91 (dd, J9 and 5 Hz, 7—H), 4.79 (d, J5 Hz, 6—H), 6.12 (s, NMe⊕).

(c) Diphenylmethyl (6R,7R)-7-[(Z)-2-(1-t-butoxycarbonylcyclobut-1-oxyimino)-2-(2-tritylaminothiazol-4-yl)-acetamido]-3-(2-methylpyrazolium-1-ylmethyl)ceph-3-em-4-carboxylate, Iodide Salt A cooled (−10°) solution of the product from stage (b) (0.600 g) in N,N-dimethylformamide (4 ml) and acetone (10 ml) was treated with potassium iodide (0.415 g) and stirred for 10 minutes. A further portion of potassium iodide (0.415 g) was added followed by acetyl chloride (0.12 ml) and the suspension was stirred at −10° to 0° for 30 minutes. The mixture was added dropwise to a solution of sodium metabisulphite (0.6 g) in water (90 ml) to give a powder which was washed with water and dried over phosphorus pentoxide to give a solid (0.58 g).

As the product contained unchanged sulphoxide the above procedure was repeated exactly (except that no dimethylformamide was used to give the title compound (0.500 g) as a powder; $\tau$(DMSO-d$_6$) 1.25 (s, Ph$_3$CNH), 1.55 (m, pyrazolium 3—H), 1.72 (m, pyrazolium 5—H), 3.15 (m, pyrazolium 4—H), 3.32 (s, thiazol 5—H), 4.15 (dd, J9 and 5 Hz, 7—H), 4.79 (d, J5 Hz, 6—H), 6.23 (s, NMe+).

(d) (6R,7R)-7-[(Z)-2-(2-Aminothiazol-4-yl)-2-(1-carboxycyclobut-1-oxyimino)acetamido]-3-(2-methylpyrazolium-1-ylmethyl)ceph-3-em-4-carboxylate The product from stage (c) (0.42 g) was treated with anisole (0.4 ml) and trifluoroacetic acid (2 ml) and left for 1 minute. The mixture was concentrated in vacuo and the residue was treated with ether to give a solid.

A suspension of this solid in anisole (0.4 ml) and trifluoroacetic acid (6 ml) was stirred for 15 minutes then filtered through a sinter and the filtrate was concentrated in vacuo to an oil.

Trituration of this oil with ether gave a gum, which was stirred in water (40 ml) and trifluoroacetic acid (10 ml) for 15 minutes at 35°. The solution was concentrated to ca 20 ml and diluted with water (30 ml). The resulting solution was washed with ether (3×60 ml) and freeze-dried to give the title compound (0.25 g), associated with about 2 moles of trifluoroacetic acid as a solid, $\lambda_{infl.}$ (pH 6 phosphate) 232 nm (E$_1$ $_{cm}$$^{1\%}$ 269), 253 nm (E$_1$ $_{cm}$$^{1\%}$ 239) and 301 nm (E$_1$ $_{cm}$$^{1\%}$ 95); $\nu_{max}$ (Nujol) 3600 to 2500 (NH$_3$+ and H$_2$O), 1792 ($\beta$-lactam) and 1730 to 1630 cm$^{-1}$ (v. broad, carbonyl groups).

EXAMPLE 3

(a) Diphenylmethyl (1S,6R,7R)-7-Formamido-3-(2-methylpyrazolium-1-ylmethyl)ceph-3-em-4-carboxylate, 1-Oxide, Bromide Salt A stirred solution of diphenylmethyl (1S,6R,7R)-3-bromomethyl-7-formamidoceph-3-em-4-carboxylate, 1-oxide (3.02 g) in N,N-dimethylformamide (5 ml) was treated at 22° with 1-methylpyrazole (2.96 g) for 23 hours. The resulting solution was added dropwise to ethyl acetate:ether=1:1 (100 ml) to give a solid which was washed with ethyl acetate and ether. The product was stirred with ethyl acetate for 1 hour, filtered off, then washed with ether to give the title compound (3.2 g) as a solid with $\nu_{max}$(Nujol), 1798 ($\beta$-lactam) and 1728 cm$^{-1}$ (CO$_2$R), $\tau$(DMSO-d$_6$) 1.42 (d, J 2 Hz, pyrazolium 3—H), 1.60 (d, J 2 Hz, pyrazolium 5—H), 3.11 (t, J 2 Hz, pyrazolium 4—H) and 3.83 (dd, J 9 and 5 Hz, 7—H).

(b) Diphenylmethyl (1S,6R,7R)-7-Amino-3-(2-methylpyrazolium-1-ylmethyl)ceph-3-em-4-carboxylate, Hydrochloride and Bromide Salts A cooled (−5°) suspension of the product of Stage (a) (2.67 g) in methanol (20 ml) was treated with phosphoryl chloride (1.28 ml). After stirring at 0° for 2 hours the suspension was filtered and the solid was washed with methanol to give starting material (1.8 g). The combined methanol extracts were added to ether (100 ml) to give a gum which was stirred with ethyl acetate to give the title compound (0.61 g) as a solid $\lambda_{max}$ (EtOH) 275 nm (E$_1$ $_{cm}$$^{1\%}$ 135), $\nu_{max}$ (Nujol), 1805 ($\beta$-lactam) and 1730 cm$^{-1}$ (CO$_2$R).

(c) Diphenylmethyl (1S,6R,7R)-7-[(Z)-2-(2-t-Butoxycarbonylprop-2-oxyimino)-2-(2-tritylaminothiazol-4-yl)acetamido]-3-(2-methylpyrazolium-1-ylmethyl)ceph-3-em-4-carboxylate 1-Oxide, Bromide Salt Phosphorus pentachloride (0.11 g) in dry dichloromethane (10 ml) at 0° was treated with the product of Preparation 4 (0.295 g) and the solution was stirred at 0° for 30 minutes. Triethylamine (0.16 ml) was added and stirring was continued at 0° for 10 minutes. The above solution was then added dropwise, over 5 minutes, to a vigorously stirred suspension of the product of stage (b) (0.303 g) in dichloromethane (15 ml) at 0°. The mixture was stirred for 3 hours at 0° to 15° and stored overnight at −20°. The resulting solution was poured into ethyl acetate (100 ml) and water (100 ml) and brine was added to disperse the emulsion. The organic phase was washed successively with water and brine then dried and evaporated in vacuo to a foam which, on trituration with ether and ethyl acetate gave the title compound (0.36 g) as a powder, $\lambda$infl (CHCl$_3$) 247 nm (E$_1$ $_{cm}$$^{1\%}$ 208), 262 nm (E$_1$ $_{cm}$$^{1\%}$ 182) and 306 nm (E$_1$ $_{cm}$$^{1\%}$ 57), $\nu_{max}$ (Nujol) 3380 (NH) and 1804 cm$^{-1}$ ($\beta$-lactam). The title compound may, if desired, be deprotected by following the procedure described in Example 1 to yield (6R,7R)-7-[(Z)-2-(2-aminothiazol-4-yl)-2-(2-carboxyprop-2-oxyimino)acetamido]-3-(2-methylpyrazolium-1-ylmethyl))ceph-3-em-4-carboxylate.

EXAMPLE 4

(a) t-Butyl (6R,7R)-3-Acetoxymethyl-7-[(Z)-2-(2-t-butoxycarbonylprop-2-oxyimino)-2-(2-tritylaminothiazol-4-yl)acetamido]ceph-3-em-4-carboxylate A stirred solution of the product of Preparation 4 (572 mg) and t-butyl (6R,7R)-3-acetoxymethyl-7-aminoceph-3-em-4-carboxylate (328 mg) in dimethylformamide (10 ml) was cooled to 0°, and 1-hydroxybenzotriazole (150 mg) was added, followed by dicyclohexylcarbodiimide (225 mg). The mixture was warmed to room temperature, stirred for 5 hours, and allowed to stand overnight. The mixture was filtered, and the white solid washed with a little ether. The filtrate and washings were diluted with water (50 ml) and extracted with ethyl acetate. The organic extracts were combined, washed successively with water, 2N hydrochloric acid, water, sodium bicarbonate solution, and saturated brine, dired and evaporated. The residue was eluted through a silica column with ether. The product-containing eluate was collected and concentrated to give the title compound (533 mg). A portion was recrystallised from di-isopropyl ether, m.p. 103° to 113° (decomp.); $[\alpha]_D^{20}+8.5°$ (c, 1.0, DMSO).

(b) (6R,7R)-3-Acetoxymethyl-7-[(Z)-2-(2-aminothiazol-4-yl)-2-(2-carboxyprop-2-oxyimino)acetamido]ceph-3-em-4-carboxylic acid Trifluoroacetic acid (18 ml) was added to a solution of the product of Stage (a) (2.4 g) in anisole (18 ml) at 0°. The mixture was stirred at room temperature for 2 hours and concentrated. The residue was dissolved in ethyl acetate and extracted with saturated sodium bicarbonate solution. The pH of the aqueous extracts was adjusted to 6, and the solution washed with ethyl acetate. The aqueous phase was acidified to pH 1.5 under ethyl acetate, saturated with sodium chloride, and extracted with ethyl acetate. The combined organic extracts were washed with saturated brine, dried and evaporated. The residue was dissolved in warm 50% aqueous formic acid (20 ml) and allowed to stand for 2 hours. The mixture was diluted with water (50 ml, and filtered. The filtrate was concentrated. The residue was taken up in water (50 ml), refiltered, and lyophilized to give the title compound (920 mg), $\lambda_{max}$ (pH 6 buffer) 236 nm ($E_{1\,cm}^{1\%}$ 250), $\lambda_{inf}$255 nm ($E_{1\,cm}^{1\%}$ 235), 296 nm ($E_{1\,cm}^{1\%}$ 103); $[\alpha]_D^{20}+20.0°$ (c 1.0, DMSO).

(c) (6R,7R)-7-[(Z)-2-(2-Aminothiazol-4-yl)-2-(2-carboxyprop-2-oxyimino)acetamide]-3-(2-methylpyrazolium-1-ylmethyl)ceph-3-em-4-carboxylate, sodium salt A mixture of the product of stage (b) (0.264 g), sodium hydrogen carbonate (0.126 g) sodium iodide (0.9 g), N-methylpyrazole (0.35 ml) and water (0.2 ml) were heated together at 80° for 1¼ hours. The resultant solution was allowed to cool, and it set solid. Water (0.5 ml) was added and the mixture was warmed until a solution was formed. This cooled solution was added to stirred acetone (100 ml). The precipitate was allowed to settle and the supernatant solution was decanted off. The precipitate was stirred with fresh acetone and was then filtered off and washed with acetone and ether and dried rapidly in vacuo to give the title compound (0.303 g) as a solid; $\tau(D_2O)$ 1.74 (m, purazolium 3—H and 5—H), 2.97 (s, thiazol 5—H), 3.16 (m, pyrazolium 4—H) and 4.10 (d, J 5 Hz, 7—H). Paper chromatography (using n-propanol:water=7.3 for development) on pH6 buffered paper indicated that the major component had the same $R_f$(ca 0.34) as that of a specimen of the title compound prepared in Example 1.

EXAMPLE 5

(a) Diphenylmethyl (1S,6R,7R)-7-[(Z)-2-(2-t-Butoxycarbonylprop-2-oxyimino)-2-(2-tritylaminothiazol-4-yl)acetamido]-3-(pyrazolium-1-yl)methylceph-3-em-4-carboxylate, 1-Oxide A solution of the product of Example (4a) (1.5 g) in N,N-dimethylformamide (7 ml) was treated with pyrazole (0.2 g) and the reaction mixture was stirred at room temperature for 24 hours. The reaction mixture was diluted with ethyl acetate (200 ml) and the organic solution was washed successively with 2N-hydrochloric acid (2×100 ml), water (2×100 ml) and brine (2×100 ml) and dried and evaporated to a foam. A solution of this foam in dichloromethane (20 ml) was subjected to preparative thin layer chromatography on silica plates using toluene:ethyl acetate:acetic acid=20:40:1 as eluant. Extraction of the appropriate bands afforded the title compound (0.736 g) as a solid with $\lambda_{max}$ (EtOH) 260 nm ($E_{1\,cm}^{1\%}$ 205) with inflections at 24 nm ($E_{1\,cm}^{1\%}$ 247), 266 nm ($E_{1\,cm}^{1\%}$ 201), 272.5 nm ($E_{1\,cm}^{1\%}$ 187) and 301 nm ($E_{1\,cm}^{1\%}$ 59), $\nu_{max}$ (Nujol) 1802 ($\beta$-lactam) and 1730 cm$^{-1}$ (C=O, esters).

(b) Diphenylmethyl (1S,6R,7R)-7-[(Z)-2-(2-t-Butoxycarbonylprop-2-oxyimino)-2-(2-tritylaminothiazol-4-yl)acetamido]-3-(2-methylpyrazolium-1-ylmethyl)ceph-3-em-4-carboxylate, 1-oxide, Iodide Salt The product of stage (a) (0.15 g) was dissolved in methyl iodide (4 ml) and the reaction mixture was stirred at room temperature for 64 hours followed by stirring at 35° for 6 days in a sealed flask.

The mixture was evaporated to dryness and the residue was triturated with ether (10 ml) and the product was filtered off, dried in vacuo and then stirred with ethyl acetate (10 ml) for 1 hour. The product was filtered off and dried in vacuo to give the title compound (0.038 g) as a solid; $\tau$(DMSO-d6) 1.48 (d, J 2 Hz, pyrazolium 3—H), 1.66 (d, J 2 Hz, pyrazolium 5—H), 2.4 to 2.8 (m, phenyl protons), 3.00 (s, CHPh$_2$), 3.11 (s, thiazol 5—H), 3.00 to 3.2 (m, pyrazolium 4—H) and 3.6 to 4.0 (m, 7—H).

The title compound may be deprotected, if desired, by following the procedure described in Example 1 to yield (6R.7R)-7-[(Z)-2-(2-aminothiazol-4-yl)-2-(2-carboxyprop-2-oxyimino)acetamido]-3-(2-methylpyrazolium-1-ylmethyl) ceph 3-em-4-carboxylate.

The antibiotic compounds of the invention may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers if necessary or with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile, pyrogen-free water, before use.

If desired, such powder formulations may contain an appropriate non-toxic base in order to improve the water-solubility of the active ingredient and/or to ensure that when the powder is constituted with water, the pH of the resulting aqueous formulation is physiologically acceptable. Alternatively the base may be present in the water with which the powder is constituted. The base may be for example an inorganic base such as sodium carbonate, sodium bicarbonate or sodium acetate or an organic base such as lysine or lysine acetate.

The antibiotic compounds may also be formulated as suppositories e.g. containing conventional suppository bases such as cocoa butter or other glycerides.

For medication of the eyes or ears, the preparations may be formulated as individual capsules, in liquid or semi-solid form, or as drops.

Compositions for veterinary medicine may also, for example, be formulated as intramammary preparations in either long acting or quick-release bases.

The compositions may contain from 0.1% upwards, e.g. 0.1–99% of the active material, depending on the method of administration. When the compositions comprise dosage units, each unit will preferably contain 50–1500 mg of the active ingredient. The dosage as employed for adult human treatment preferably ranges from 250 to 6000 mg per day, depending on the route and frequency of administration. For example, in adult human treatment 1000 to 3000 mg per day administered intravenously or intramuscularly should normally suffice. In treating Pseudomonas infections higher daily doses may be required.

The antibiotic compounds according to the invention may be administered in combination with other therapeutic agents such as antibiotics, for example penicillins or other cephalosporins.

The following formulations illustrate how the compounds according to the invention may be made up into pharmaceutical compositions.

A: Formulation—For injection

Formula Per Vial

| | |
|---|---|
| (6R,7R)-7-[(Z)-2-(2-Aminothiazol-4-yl)-2-(2-carboxyprop-2-oxyimino)acetamido]-3-(2-methylpyrazolium-l-ylmethyl) ceph-3-em-4-carboxylate | 500 mg |
| Sodium Carbonate, anhydrous | 120 mg |

Method

Blend the sterile cephalosporin antibiotic with sterile sodium carbonate under aseptic conditions. Fill aseptically into glass vials under a blanket of sterile nitrogen. Close the vials using rubber discs, or plugs, held in position by aluminium overseals, thereby preventing gaseous exchange or ingress of microorganisms. Constitute the product by dissolving in Water for Injections or other suitable sterile vehicle shortly before administration.

B: Formulation—For Injection

Fill sterile (6R,7R)-7-[(Z)-2-(2-Aminothiazol-4-yl)-2-(1-carboxycyclobut-1-oxyimino)acetamido]-3-(2-methylpyrazolium-1-ylmethyl) ceph-3-em-4-carboxylate monosodium salt into glass vials, such that each vial contains an amount equivalent to 1.00 g of the antibiotic acid. Carry out the filling aseptically under a blanket of sterile nitrogen. Close the vials using rubber discs, or plugs, held in position by aluminium overseals, thereby preventing gaseous exchange or ingress of microorganisms. Constitute the product by dissolving in Water for Injections or other suitable sterile vehicle shortly before administration.

We claim:

1. A cephalosporin antibiotic selected from the group consisting of compounds of the formula:

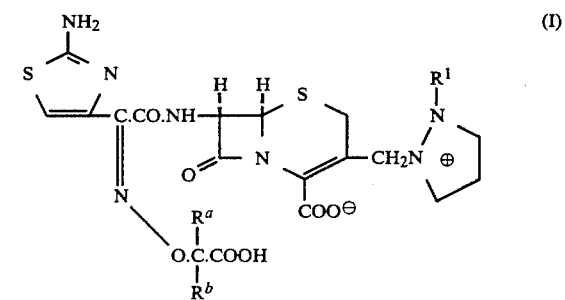

wherein
$R^1$ and $R^b$, which may be the same or different, each represents a $C_{1-4}$ alkyl group, or together with the carbon atom to which they are attached form a $C_{3-7}$ cycloalkylidene group and
$R^1$ represents a $C_{1-4}$ alkyl group and non-toxic salts thereof.

2. A compound as claimed in claim 1 wherein $R^a$ and $R^b$ each represents a methyl group.

3. A compound as claimed in claim 1 wherein $R^a$ and $R^b$ together with the carbon atom to which they are attached form a $C_{3-5}$ cycloalkylidene group.

4. A compound as claimed in claim 1 wherein $R^1$ represents a methyl group.

5. A compound as claimed in claim 1 which is (6R,7R)-7-[(Z)-2-(2-aminothiazol-4-yl)-2-(2-carboxyprop-2-oxyimino)acetamido]-3-(2-methylpyrazolium-1-ylmethyl) ceph-3-em-4-carboxylate.

6. A non-toxic salt of the compound claimed in claim 5.

7. A compound as claimed in claim 1 which is (6R,7R)-7-[(Z)-2-(2-aminothiazol-4-yl)-2-(1-carboxycyclobut-1-oxyimino)acetamido]-3-(2-methylpyrazolium-1-ylmethyl) ceph-3-em-4-carboxylate.

8. A non-toxic salt of the compound claimed in claim 7.

9. A pharmaceutical composition for use in human or veterinary medicine comprising an effective amount of at least one antibiotic compound of claim 1 in association with a pharmaceutical carrier or excipient.

10. A method of combatting a bacterial infection in a human or a warm blooded animal comprising administering an antibacterially effective amount of at least one compound of claim 1.

* * * * *